United States Patent [19]

Malilay

[11] Patent Number: 5,522,828
[45] Date of Patent: Jun. 4, 1996

[54] SURGICAL KNIFE WITH BLADE SHIELD

[76] Inventor: Cicero H. Malilay, 3838 Vinton Ave., Apt. 107, Culver City, Calif. 90232

[21] Appl. No.: 336,000

[22] Filed: Nov. 8, 1994

[51] Int. Cl.[6] .......................... A61B 17/32; B26B 03/06; B26B 01/00
[52] U.S. Cl. .............. 606/167; 30/153; 30/329; 30/339
[58] Field of Search .................. 606/167, 172, 606/185; 27/24.1; 30/123.7, 136, 142, 143, 146–151, 153–156, 329, 337, 339

[56] References Cited

U.S. PATENT DOCUMENTS

| 4,137,631 | 2/1979 | Pickett et al. ........................ 30/329 |
| 5,055,106 | 10/1991 | Lundgren ........................... 606/167 |
| 5,250,064 | 10/1993 | Schneider .......................... 30/151 |
| 5,330,493 | 7/1994 | Haining ............................. 606/167 |
| 5,330,494 | 7/1994 | Westhvizen et al. ................. 606/167 |

*Primary Examiner*—Stephen C. Pellegrino
*Assistant Examiner*—Glenn Dawson
*Attorney, Agent, or Firm*—Linval B. Castle

[57] ABSTRACT

A scalpel with a blade set at about thirty degrees to the handle has a blade shield that pivots up from the handle and a shield lock that prevents accidental lifting of the shield. The shield lock includes a small movable shaft just below the sidewalls of the shield next to the handle. A small disc is at each end of the shaft close to the handle and prevents the shield from being pivoted up. A counterbore around the shaft on one side of the handle enables the adjacent disc to be pushed in, thus extending the opposite disc permitting the shield to be pivoted up to unshield the blade.

5 Claims, 2 Drawing Sheets

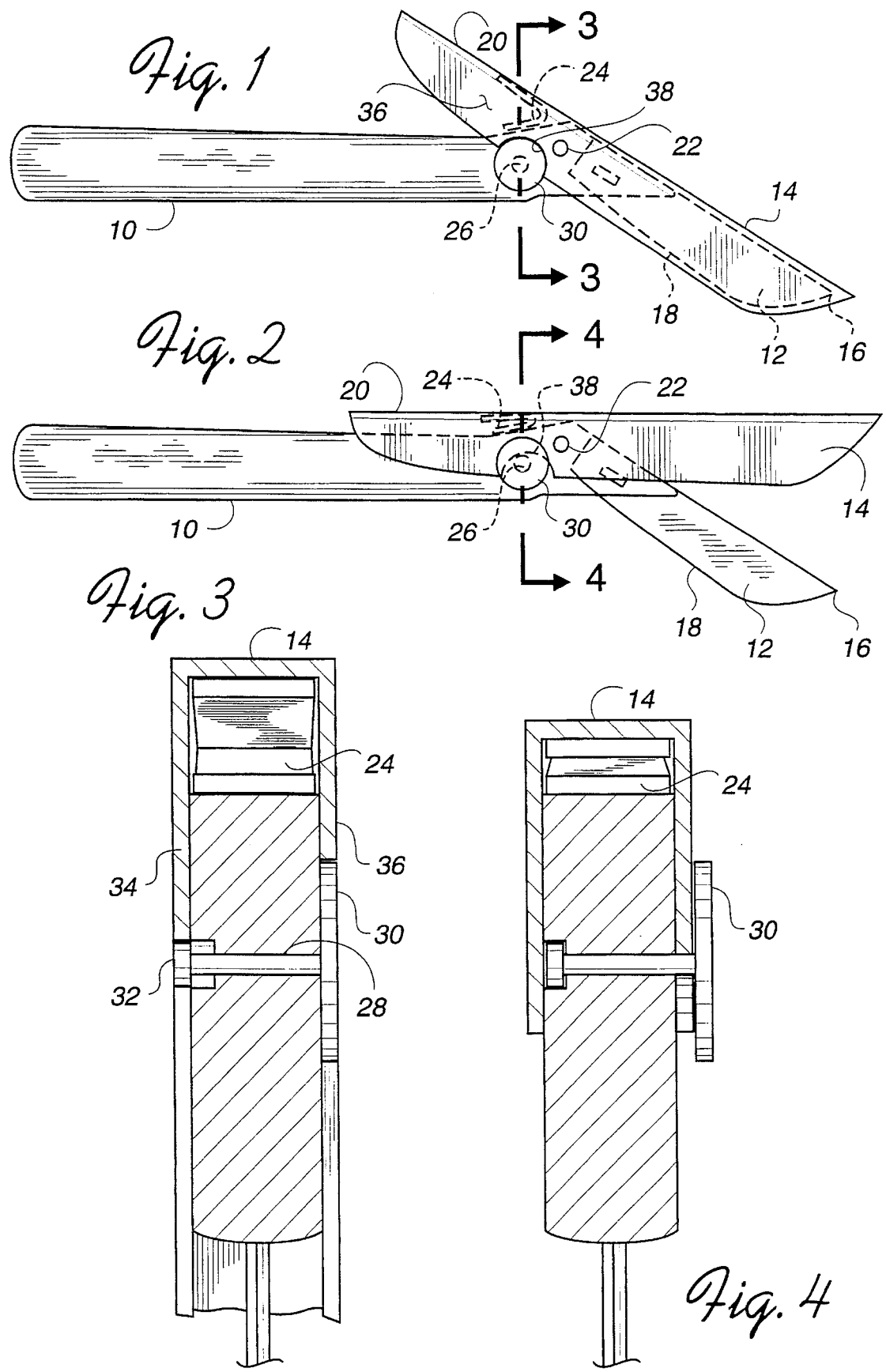

SURGICAL KNIFE WITH BLADE SHIELD

This invention relates to surgical instruments and in particular to a scalpel having an angled blade with a locking protective cover.

BRIEF SUMMARY OF THE INVENTION

The great majority of surgical knives comprise a handle with an in-line attached or attachable blade and is not only used in surgical procedures but also in biological and other laboratories, In most instances, the user will conveniently hold the handle between thumb and forefinger, much as he would hold a pen. In order to minimize accidental "sticking" and possible contamination by the blade, a blade is often covered with a removable shield that is quickly and easily removable and which may be sterilized along with the blade. If a blade shield is to be a part of the surgical knife, such as described and claimed in U.S. Pat. No. 5,250,064, the shield is normally pivoted from the blade by pressure from the forefinger.

There are many instances when surgeons, students and laboratory technicians would find a scalpel with the blade at an angle to the handle to be more convenient and accurate than the in-line blade, for example in very close work. The surgical knife of the invention is of this type. In addition, to prevent accidental "sticks" or cuts from the blade and the possibility of spreading an infectious disease, the surgical knife of the invention also has a convenient blade shield which is normally locked down in place over the blade and which can only be released by intentionally pressing a button on the side of the knife handle.

DESCRIPTION OF THE DRAWINGS

In the drawings which illustrate a preferred embodiment of the invention:

FIG. 1 is a side elevational view of the surgical knife with the blade shield locked over the blade;

FIG. 2 is a side elevational view illustrating the shield unlocked and lifted for use;

FIG. 3 is a section taken along the lines 3—3 of FIG. 1 showing the locking mechanism;

FIG. 4 is a section taken along the lines 4—4 of FIG. 2;

DETAILED DESCRIPTION OF THE PREFERRED EMBODIMENT

Figure 5:
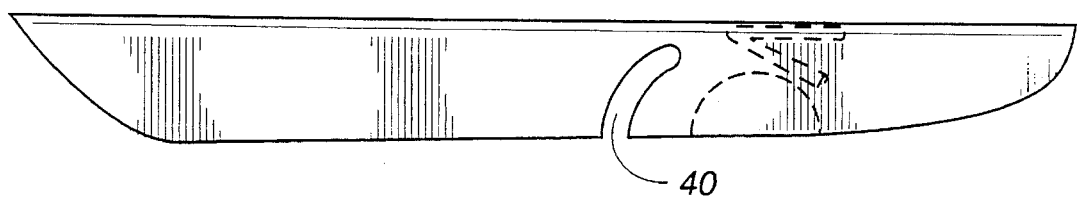
FIG. 5 illustrates an alternate embodiment of the blade shield.

Illustrated in FIG. 1 is a scalpel comprising a handle 10 and a conventional removable scalpel blade 12 which is at an angle of approximately thirty degrees to the longitudinal axis of the handle. This angled blade is very convenient to use, particularly for very close work. The blade is protected by a shield 14 which surrounds both sides and top of the blade with the sides of the shield extending down to protect inadvertent touching of the blade point 16 or sharp edge 18. As shown in FIG. 1, the shield extends up over the handle 10 to form a finger control portion 20 which raises the shield from the blade as will be subsequently described. The shield is thick since is must also cover part of the handle 10 but the thin sheet stainless steel of the shield may be pressed together to narrow the shield near the blade edge 18 and point 16.

The shield 14 is normally locked down over the blade 12 and may be pivoted up around pivot point 22 which comprises a small pin extending laterally through the handle 10 and both sides of the shield 14. When the shield is pivoted up by depressing the finger control portion 20, the entire blade 12 is revealed, as shown in FIG. 2. A small spring 24 is positioned under the shield, between the shield and the top of the handle 10, and operates to return the shield down to cover the blade upon release of the finger control portion 20.

As an additional safety feature, the surgical knife of the invention is also provided with a lock 26 which may conveniently be used to lock the shield down to cover the blade. The lock 26 is best illustrated in FIGS. 3 and 4 which are sectional views taken along the lines 3—3 and 4—4 of FIGS. 1 and 2, respectively. The lock comprises a small shaft 28 laterally extending through a hole through the handle, behind the pivot point 22 and near the central axis of the handle. One end of the shaft 28 is attached to the center of a disc 30 of about a half inch in diameter, the opposite end of the shaft is attached to the center of a smaller disc 32, about a quarter inch in diameter. The overall length of the shaft 28 with attached discs 30, 32 substantially equals the thickness of the handle 10 plus the thickness of the sidewalls 34, 36 of the shield 14, as shown in FIG. 3, but the shaft and discs may slide so that the small disc 32 becomes recessed into a counterbore in the handle and the large disc is extended from the side surface of the handle.

The discs 30, 32 cooperate with the shape of the shield to provide the safety lock. Referring back to FIG. 1, the sidewall 36 of shield 14 has a semicircular opening 38 of the same or slightly larger diameter than the large disc 30 and coaxial with disc 30 when the shield covers the blade, as shown. With the disc 30 positioned against the side of the handle, as shown in FIG. 3, the disc 30 is located within that semicircular opening 38 and is prevented from being pivoted about its pivot 22. The smaller disc extending from the opposite sidewall 34 is in contact with the lower edge of the sidewall and also adds to the prevention.

A slight thumb pressure against the smaller disc 32 will force the disc into the counterbore and will force the large disc 30 out from the handle so that the sidewall 36 of shield 14 will fall behind the extended large disc and the recessed small disc will be out of the path of the opposite sidewall 34, as shown in FIG. 4. This unlocks the shield and enables the it to be raised with a slight pressure of the forefinger on top of the finger control portion 20 of the shield.

Conversely, when finished using the blade, the forefinger is removed from the finger control portion 20 to lower the shield and merely moved over to depress the large disc 30 to lock the shield. A left handed person would use his thumb on the large disc 30.

Figure 6:
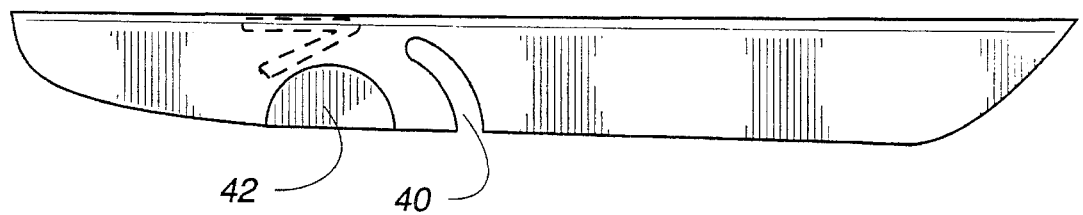
FIG. 6 illustrates the opposite side of of the embodiment of FIG. 5.

FIGS. 5 and 6 illustrate the left side and right side, respectively, of an alternate shield which operates in the identical manner of the shield 14 but which is removable from a handle. The alternate shield has an arcuate slot 40 on each side of the shield beginning at the lower edge of the shield sidewall forward of the position of the shield lock 42 and extends back toward the finger control portion to the point of engagement of the pivot pin extending laterally through the handle.

I claim:

1. A scalpel comprising:

a substantially straight elongated handle having first and second spaced side members and first and second ends;

a blade attached to the first end of said handle, said blade being at an angle of approximately thirty degrees to said handle;

blade shield having sidewalls for shielding the blade in said said sidewalls extending back from said blade to closely overlie the side members at the first end of said handle, said shield being pivotally coupled to said handle by a pivot rod passing laterally through said handle at said first end; and a shield lock in said handle for preventing the accidental unshielding of said blade.

2. The scalpel claimed in claim 1 further including a spring between said handle and said shield for biasing said pivoted shield to completely shield said blade.

3. The scalpel claimed in claim 2 wherein said shield has a finger control portion overlying said handle.

4. The scalpel claimed in claim 1 wherein said shield lock includes:

a small shaft laterally moveable through said handle, said shaft having a first end coupled to a first disc and having a second end coupled a second disc, said first and second discs nomally closely overlying the side members of said handle;

a counterbore in said second side of said handle, said counterbore coaxial with said small shaft and being of sufficient depth and diameter to receive the adjacent second disc; and a portion of said shield sidewall adjacent said first disc being removed to receive said first disc closely overlying its adjacent first side member when said shield is in a shielding position, said first disc being forced away from its adjacent first side member to release said shield when said second disc is in its counterbore.

5. In combination with a knife handle having first and second spaced sides, said handle supporting by lateral pivots a blade shield having sidewalls closely overlying said first and second sides, a lock for preventing the accidental unshielding of a blade on said handle, said lock comprising:

a small shaft laterally moveable through said handle, said shaft having a first end coupled to a first disc and a second end coupled to a second disc, said first and second discs closely overlying the sides of said handle;

a counterbore in the second side of said handle, said counterbore coaxial with said small shaft and being of sufficient depth and diameter to receive the adjacent second disc; and a portion of said shield sidewall adjacent said first disc being removed to receive said first disc closely overlying the first side of said handle when said shield is in a shielding position, said first disc being forced away from the first side of said handle to release said shield when said second disc is in said counterbore.

* * * * *